US006911558B2

(12) United States Patent
Bowman et al.

(10) Patent No.: US 6,911,558 B2
(45) Date of Patent: Jun. 28, 2005

(54) METHOD FOR PURIFYING CHLOROMETHYL CHLOROFORMATE

(75) Inventors: Mark P. Bowman, New Kensington, PA (US); Charles B. Kreutzberger, Harrison City, PA (US)

(73) Assignee: PPG Industries Ohio, Inc., Cleveland, OH (US)

( * ) Notice: Subject to any disclaimer, the term of this patent is extended or adjusted under 35 U.S.C. 154(b) by 169 days.

(21) Appl. No.: 10/358,593

(22) Filed: Feb. 5, 2003

(65) Prior Publication Data

US 2004/0152911 A1 Aug. 5, 2004

(51) Int. Cl.[7] ............................................. C07C 51/58
(52) U.S. Cl. ....................... 562/840; 562/864; 562/856
(58) Field of Search ............................ 562/226, 129; 558/280, 283

(56) References Cited

U.S. PATENT DOCUMENTS

| | | | |
|---|---|---|---|
| 4,592,872 A | 6/1986 | Cagnon et al. | 558/281 |
| 4,592,874 A | 6/1986 | Cagnon et al. | 558/283 |
| 4,622,431 A | 11/1986 | Briody et al. | 568/606 |
| 4,714,785 A | 12/1987 | Manner | 568/614 |
| 4,734,535 A | 3/1988 | Greif et al. | 570/261 |
| 4,814,524 A | 3/1989 | Briody et al. | 570/201 |
| 5,712,407 A | 1/1998 | Kreutzberger et al. | 558/283 |

FOREIGN PATENT DOCUMENTS

| | | | | |
|---|---|---|---|---|
| DE | 32 41 568 | 5/1983 | | C07C/69/96 |
| DE | 38 26 584 | 2/1989 | | C07C/69/96 |
| FR | 2 621 913 | 8/1989 | | C07C/69/96 |
| JP | 3050741 B2 | 6/2000 | | E21F/13/02 |

OTHER PUBLICATIONS

Blasser, Jane E., "Synthesis And Uses of Pure Chloromethyl Chloroformate And An Economical Ne Route to Trichloroacryloyl Chloride", 1993, UMI Dissertation Services.

"March's Advanced Organic Chemistry, Reactions, Mechanisms and Structures", 5th Edition, M.B. Smith and J. March, Wiley–Interscience, 2001, pp. 105–109.

"2,2–Dichlorovinyl Choloroformate", Mark P. Bowman and R. A. Olofson; *Journal of Organic Chemistry*, 1990, vol. 55, pp. 2240–2243.

"An Efficient Synthesis of Some Substituted Vinylic Cholorformates: Reaction Scope And Limitations", Mark P. Bowman, Jean–Pierre G. Senet, Thierry Malfroot and R. A. Olofson; *Journal of Organic Chemistry*, 1990, vol. 55, pp. 5982–5986.

*Primary Examiner*—Johann Richter
*Assistant Examiner*—Karl Puttlitz
(74) *Attorney, Agent, or Firm*—Linda Pingitore

(57) ABSTRACT

Describes a method for obtaining substantially pure chloromethyl chloroformate from a chloroformate mixture comprising chloromethyl chloroformate and methyl chloroformate by heating the chloroformate mixture in a reaction zone at temperatures ranging from at least 50° C. to the reflux temperature of the chloroformate mixture in the reaction zone while simultaneously removing volatile gaseous decomposition products from the reaction zone. Dichloromethyl chloroformate may also be present in the chloroformate mixture.

48 Claims, No Drawings

METHOD FOR PURIFYING CHLOROMETHYL CHLOROFORMATE

DESCRIPTION OF THE INVENTION

The present invention relates to chloromethyl chloroformate. In particular, the present invention relates to a method of recovering substantially pure chloromethyl chloroformate from a chloroformate mixture comprising chloromethyl chloroformate, and methyl chloroformate. The chloroformate mixture may in addition contain dichloromethyl chloroformate, and may also contain trichloromethyl chloroformate.

More particularly, the present invention comprises a method of recovering substantially pure chloromethyl chloroformate from said chloroformate mixture by the steps of heating the mixture in a reaction zone in the presence of a nucleophilic catalyst while simultaneously removing volatile gaseous decomposition products resulting from the heating step, particularly hydrogen chloride, and subsequently recovering from said reaction zone substantially pure chloromethyl chloroformate product. The chloromethyl chloroformate product recovered is substantially free of methyl chloroformate. When dichloromethyl chloroformate and/or trichloromethyl chloroformate are present in the starting chloroformate mixture, the chloromethyl chloroformate product is also substantially free of dichloromethyl chloroformate and trichloromethyl chloroformate.

A number of specialty chemicals are produced using chloromethyl chloroformate as a building block. In particular, chloromethyl chloroformate is used to prepare carbonate derivatives that are used in the pharmaceutical industry, the agrochemical industry and the photoresist industry. Chloromethyl chloroformate can be prepared by the catalytic photochlorination of methyl chloroformate or methyl formate (which first yields methyl chloroformate.) This process commonly produces a chloroformate mixture comprising at least two, and possibly three, chlorinated products of methyl chloroformate; namely, chloromethyl chloroformate (CMC), dichloromethyl chloroformate (DCMC) and trichloromethyl chloroformate (TCMC) because the chlorination rates for these three chlorinated materials are not very different. See Ullmann's Encyclopedia of Industrial Chemistry. Unreacted methyl chloroformate (MCF) in the chloroformate mixture can be separated easily from the chlorinated reaction products by distillation, but the boiling points of the chlorinated reaction products, e.g., CMC and DCMC (ca 106° C. and 111° C.) are too close to allow a clean separation.

German Offenlegenschrift 3,241,568 (May 19, 1983) describes the reaction of formaldehyde and phosgene to prepare CMC; however, the reaction is not clean because of problems involving the thermal depolymerization of paraformaldehyde and the facile reversal of that process. [See also Chem. Abstr. 1983, 99, 53164g.] German Offenlegenschrift 3,826,584 (Feb. 16, 1989) describes a process for manufacturing CMC comprising 23 chlorination, distillation and recycling steps. [See also Chem. Abstr. 1989, 111, 117289c and French Demande 2,621,913 (Aug. 21, 1989).] However, the product is reported by Blasser (cited below) to contain 3% of the dichlorinated product, i.e., DCMC.

The purification of chloromethyl chloroformate (CMC) from a mixture containing methyl chloroformate and dichloromethyl chloroformate by decomposing the dichloromethyl chloroformate (and any diphosgene) over benzyltributyl ammonium chloride (BTBAC) or hexabutyl guanidinium chloride hydrochloride at 70° C. has been described. See, Blasser, Jane E., "Synthesis and Uses of Pure Chloromethyl Chloroformate and an Economical New Route to Trichloroacryloyl Chloride", a thesis submitted in partial fulfillment of the requirements for the degree of Doctor of Philosophy in December 1993 to The Pennsylvania State University, Department of Chemistry. Under the conditions described in the thesis, dichloromethyl chloroformate decomposes to phosgene, hydrogen chloride and carbon monoxide. Subsequent distillation of the crude product from the catalyst mixture is used to produce chloromethyl chloroformate in purities of from 86 to 97%. No destruction of methyl chloroformate under the described conditions is described or noted by Blasser.

It would be a significant economic benefit if substantially pure chloromethyl chloroformate could be produced without the need for a distillation step to separate it from methyl chloroformate. It has now been discovered that substantially pure chloromethyl chloroformate can be recovered from a chloroformate mixture comprising methyl chloroformate and chloromethyl chloroformate without a distillation step by (1) heating the crude chloroformate mixture in a reaction zone in the presence of a nucleophilic catalyst at temperatures of at least 50° C., more typically from 70 ° C. or 80° C. to the reflux temperature of the mixture, and (2) simultaneously removing from the reaction zone volatile gaseous decomposition products resulting from the catalytic heating step, e.g., carbon monoxide, hydrogen chloride and other low boiling gases. The substantially pure chloromethyl chloroformate recovered from this process is substantially free of methyl chloroformate and is also substantially free of dichloromethyl chloroformate and trichloromethyl chloroformate, if such polychlorinated chloroformates are present in the treated crude chloroformate mixture.

DETAILED DESCRIPTION OF THE INVENTION

As used in this description and claims, all values expressing percentages, ratios, ranges, amounts, temperatures, pressures, etc., other than in the enumerated operating examples or where otherwise indicated, are to be understood as modified in all instances by the term "about".

Chloromethyl chloroformate is commonly produced by the catalytic chlorination, e.g., photochlorination, of methyl chloroformate. As noted by Blasser (cited above—paragraph bridging pages 3 and 4), this process yields a crude mixture including the unreacted starting material and the three possible chlorinated products because the chlorination rates are not very different. Blasser suggests that by stopping the reaction after adding less than one equivalent of chlorine, the generation of diphosgene ($Cl_3COCOCl$) can be avoided and the formation of dichloromethyl chloroformate ($Cl_2CHOCOCl$) minimized. However, as noted, the crude reaction mixture also contains unreacted methyl chloroformate. Hence, the crude reaction mixture comprises unreacted methyl chloroformate, the desired chloromethyl chloroformate, dichloromethyl chloroformate and perhaps some trichloromethyl chloroformate (diphosgene). Stated differently, the desired chloromethyl chloroformate product contains contaminating quantities of methyl chloroformate, dichloromethyl chloroformate and possibly trichloromethyl chloroformate.

In accordance with an embodiment of the present invention, substantially pure chloromethyl chloroformate is recovered from a chloroformate mixture comprising chloromethyl chloroformate and methyl chloroformate. In accordance with another embodiment of the present invention, substantially pure chloromethyl chloroformate is recovered from a chloroformate mixture comprising chloromethyl chloroformate, methyl chloroformate (MCF) and dichloromethyl chloroformate (DCMC). Trichloromethyl chloroformate (TCMC) may also be present in each of the mentioned chloroformate mixtures. By substantially pure chloromethyl chloroformate (CMC) is meant that the product recovered from the crude chloroformate mixture contains at least 95% CMC. Typically, the recovered product contains at least 98% CMC. Further, the product contains less than 5%, typically less than 1% MCF; and less than 2%, typically less than 1% DCMC. More typically, the CMC product contains less than 0.2% of each of MCF, DCMC and TCMC. All of the aforementioned percentages are area percents, as determined by gas chromatography (GC) using a thermal conductivity detector (TCD).

The amount of MCF, DCMC and TCMC in the crude chloroformate mixture will vary, and will depend on the mole ratio of the reactants and the chlorination conditions used to chlorinate the starting methyl chloroformate. Generally, the crude chloroformate mixture will contain less than 35 percent MCF, e.g., from 5 to 30% of MCF; less than 40 percent DCMC, e.g., from 2 to 35% of DCMC, and usually not more than 1 percent of TCMC, e.g., from 0 to 1% of TCMC. More typically, the crude chloroformate mixture will contain from 10 to 25 percent of MCF, from 15 to 30 percent DCMC, and not more than 0.2 percent of TCMC. All of the aforementioned percentages are area percents, as determined by gas chromatography (GC) using a TCD. Such area percents correspond reasonably well with weight percentages.

In accordance with an embodiment of the present invention, the crude chloroformate mixture is heated in a suitable vessel at temperatures of at least 50° C. at pressures of from 50 to 90 Torr (6.6 to 12 kPa). Typically, at atmospheric pressure, the temperature at which the crude chloroformate mixture is heated varies from 70° C. to the reflux temperature of the crude chloroformate mixture in the reaction vessel, i.e., from 92 to 110° C. The reflux temperature will vary depending on the pressure within the reaction zone, i.e., atmospheric or sub-atmospheric pressures, the particular composition of the crude chloroformate mixture charged to the reaction vessel, and also on the changing composition of the chloroformate mixture remaining in the reaction vessel as various components of the mixture are destroyed and vaporous decomposition products are removed from the reaction vessel. As is well known to those skilled in the art, the higher the temperature in the reaction zone, the faster will be the decomposition rate at which contaminating products in the crude chloroformate mixture are destroyed. It is also well known to those skilled in the art that a combination of lower temperatures and reduced pressures can be used to assist in the removal of low boiling volatiles from the chloroformate mixture in the reaction zone. A pressure ranging from 50 Torr (6.6 kPa) to above atmospheric pressure can be employed.

In a further embodiment of the present invention, the temperature to which the crude chloroformate mixture is heated can vary from 50° C. to the reflux temperature of the chloroformate mixture in the reaction vessel, i.e., from 92° C. to 110° C., e.g., 106° C., particularly from 86° C. to 100° C. Pressure within the reaction vessel can range from 50 Torr (6.6 kPa) to greater than 1 bar (100 kPa). The temperatures and pressures used in the process described can each be selected between any combination of the aforementioned temperatures and pressures, inclusive of the specifically recited temperatures and pressures, provided that the combination of temperature and pressure selected produces the desired decomposition of the contaminating amounts of MCF and, if present, DCMC and TCMC—desirably in an economic time frame. Generally, lower temperatures, particularly temperatures below 70° C. will require pressures below atmospheric pressure.

The period of time that the crude chloroformate mixture is held at the selected temperature and pressure within the aforedescribed temperature and pressure ranges will vary and will depend on (1) the temperature chosen since the heating time is an inverse function of the temperature, i.e., the higher the temperature, the shorter the time required (and vice versa), (2) the catalyst chosen, since some catalysts are more active than others, (3) the amount of contaminants, e.g., MCF and DCMC, that it is desired be removed, and (4) whether means are employed to expedite the removal of the volatile gaseous decomposition products from the reaction vessel, e.g., inert gas sparging, sub-atmospheric pressure (vacuum) conditions within the reaction vessel, etc. The length of the heating time is not critical, i.e., it is not an important variable of the described process, although it would be important for economic considerations. Generally, the heating time will extend for the period required to reach the minimum level of impurities desired, i.e., the level of impurities that can be tolerated for the use to which the CMC product is to be put, or until the level of impurities, e.g., MCF and DCMC, are not detectable by GC analysis. The period of heating can range from as little as 15 minutes to as much as 17 hours. Typically, the period will range from 30 minutes to 5 hours, more particularly from 45 minutes to 2 or 3 hours. The heating period can range between any combination of the aforementioned times inclusive of the specifically recited times.

In accordance with an embodiment of the process of the present invention, vaporous decomposition products, most notably hydrogen chloride, and low boiling volatiles, such as carbon monoxide, carbon dioxide and phosgene, are removed from the vessel in which the crude chloroformate mixture is heated, i.e., from the reaction zone within a suitable reaction vessel, while the crude chloroformate mixture is undergoing heating in the presence of the nucleophilic catalyst. As described by Blasser (cited above), dichloromethyl chloroformate decomposes to phosgene, hydrogen chloride and carbon monoxide when heated over a catalyst such as benzyl tributyl ammonium chloride (BTBAC) or hexamethyl guanidinium chloride hydrochloride (HMGCl-HCl). Methyl chloroformate decomposes to methyl chloride and carbon dioxide under the described conditions. In one embodiment of the present invention, the aforementioned gaseous decomposition products at the conditions encountered in the reactor are removed from the reaction zone, and more particularly from the reactor itself. In a particular embodiment of the present invention, at least hydrogen chloride gas is removed from the reaction zone since it is believed that hydrogen chloride inhibits the decomposition of methyl chloroformate.

The volatile gaseous products present and/or generated within the reactor during the heating step can be removed from the reaction zone, more typically from the reaction vessel itself, by methods or combination of methods known to those skilled in the art. Conventionally, the reactor is equipped with a condenser, e.g., a water-cooled condenser, scrubber, and/or thermal oxidizer for condensing and treating (neutralizing) toxic gaseous products emanating from the reactor during the described process. In such an arrangement, phosgene and HCl gas are allowed to pass through the condenser to the scrubber and/or thermal oxidizer, while liquid condensate is returned to the reactor. As some of the gas decomposition products are toxic, e.g., phosgene and hydrogen chloride, and condensing systems are not perfect, a scrubber is used to neutralize such toxic gases, i.e., phosgene and HCl. In the scrubber, the toxic gases are contacted with an aqueous alkaline solution, such as aqueous ammonium hydroxide, sodium or potassium hydroxide, an amine, etc. Gases, such as carbon monoxide or carbon dioxide, can be released to the environment after passing through a scrubber or a thermal oxidizer.

In one embodiment, the crude chloroformate mixture is heated to reflux temperatures. At such temperatures, volatile gas decomposition products readily move from the crude chloroformate mixture to the top of the reactor and thence through the condenser, scrubber, etc. In another embodiment, sub-atmospheric pressures, i.e., a vacuum, are imposed on the reactor, e.g., by use of a vacuum pump downstream of the scrubber, thereby lowering the pressure within the reactor and further increasing the volatility of the low boiling components. When a vacuum is imposed on the reactor, the pressure is less than atmospheric, i.e., 14.7 pounds per square inch (at standard conditions) (101 kPa). Such sub-atmospheric pressures can range from 6.6 kPa (50 Torr) to 95 kPa (720 Torr).

In another embodiment, a chemically inert gas is introduced into the reactor to assist in the removal of the gaseous products of decomposition from the reactor. The gas can be introduced into the reactor in the space above the crude chloroformate mixture and/or below the liquid surface of the crude chloroformate mixture, i.e., a gas sparge can be used to help carry the gaseous products of decomposition from the body of the liquid reaction mixture to and through the condenser, scrubber, etc.

The gas used in the foregoing embodiment should be chemically inert, i.e., it should not be reactive with any of the chloroformates in the crude chloroformate mixture or with any of the vapors removed from the reaction zone under the conditions used in the process. Suitable inert gases that can be used include, but are not limited to, nitrogen, carbon dioxide, carbon monoxide argon, natural gas, etc. The amount of inert gas used is not a variable of the process, but should be sufficient to enhance the removal of the vapors produced in the reactor. Too large a quantity of inert gas will be an economic drawback because of the cost of the inert gas and the equipment needed to handle the inert gas exiting from the reactor, particularly if the inert gas is to be treated and recycled to the reactor. The inert gas should be substantially dry, i.e., be substantially free of water, because water will react with chloroformates.

In one embodiment of the present invention, only heat, e.g., reflux temperatures, is used to promote the removal of gas decomposition products from the reactor. In another embodiment, heat and an inert gas sparge are used in combination. In further embodiments, heat and sub-atmospheric pressure (vacuum) or heat, sub-atmospheric pressure, and an inert gas sparge are used in combination. Any combination of the aforementioned recited means (and other means known to those skilled in the art) to promote and/or assist removal of the gaseous decomposition products from the reaction zone can be used.

In accordance with the process of the present invention, a crude chloroformate mixture, as described above, is heated in the presence of a nucleophilic catalyst. As used herein, the term "catalyst" is meant to include a material that does not participate directly in the decomposition reaction(s), is used in relatively small amounts, i.e., catalytic amounts (but less than equivalent amounts) compared to the chloroformates in the starting crude mixture, and catalyzes the decomposition of methyl chloroformate and, when present, higher chlorinated chloroformates, such as dichloromethyl chloroformate and trichloromethyl chloroformate. In some cases, the catalyst can be recovered from the chloromethyl chloroformate end product by methods known to those of ordinary skill in the art and reused. The catalyst can be a liquid or a solid, and may be soluble in the crude chloroformate mixture. The catalyst, if not soluble in the crude chloroformate mixture, is dispersible in the mixture.

By the term "nucleophilic" is meant a material that is capable of reacting with the chloroformate mixture in a manner that results in the release of a labile chloride anion. The nucleophilic catalyst can be a salt that has an anion capable of attacking the carbonyl group of a chloroformate. The cation of such a salt is one that allows the anion to be mobile so that it can carry out the nucleophilic attack. The salt can be an inorganic or organic salt. Generally, the salt is a quaternary ammonium or phosphonium salt, e.g., a chloride salt.

In one embodiment, the quaternary organic catalyst salt can be represented by the expression:

$$(Y_aH_{(4-a)}M)^+X^- \qquad \qquad I$$

wherein M is nitrogen or phosphorus; Y is the organic portion of the salt molecule bonded to M by covalent linkages, e.g., four independent monovalent aliphatic hydrocarbon groups, a is a number of from 1 to 4, and $X^-$ is a monovalent anion associated with the cation, $(Y_aH_{(4-a)}M)^+$.

The organic quaternary salts can be more graphically illustrated by the following formulae:

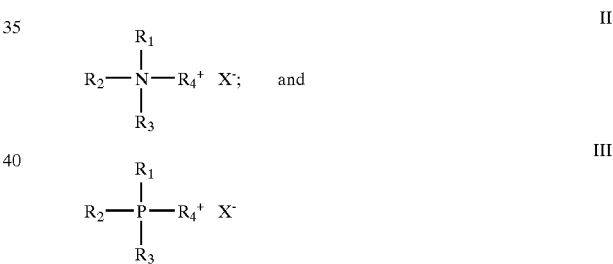

wherein $R_1$, $R_2$, $R_3$ and $R_4$ (Y in formula I) are each monovalent hydrocarbon groups containing from 1 to 25 carbon atoms, as for example, $C_1$–$C_{20}$ alkyl groups; $C_5$–$C_6$ cycloalkyl groups; aryl groups such as phenyl and p-tolyl; or alkylaryl groups such as phenyl-substituted alkyl groups containing from 1 to 4 carbon atoms, e.g., benzyl, phenethyl, phenpropyl and phenbutyl; and X is a monovalent anion, such as a halide ion, i.e., chloride, bromide or iodide, the hydrogen sulfate anion ($HSO_4$), the hydroxyl anion ($OH^-$), the dihydrogen phosphate anion ($H_2PO_4^-$), and the hydrogen phosphate anion ($HPO_4^=$). The organic quaternary salts may also be depicted herein by the expressions $(R_1R_2R_3R_4N)^+ X^-$, and $(R_1R_2R_3R_4P)^+ X^-$.

The number of carbon atoms in each of the hydrocarbon substituents, $R_1$, $R_2$, $R_3$ and $R_4$ can vary considerably. Each can contain from 1 to 25 or more carbon atoms. Typically, each hydrocarbon group will contain from 1 to 18 carbon atoms. In the case of certain alkyl hydrocarbon groups containing 8 or more carbon atoms, the number of carbon atoms in the group may be an average number, i.e., the hydrocarbon groups contains a distribution of alkyl groups of varying carbon length.

The total carbon atom content of all of the groups, $R_1$, $R_2$, $R_3$ and $R_4$, will in one embodiment be at least 12. The upper limit of the number of carbon atoms will depend on economic and other practical factors. An upper total limit of 40 carbon atoms is a practical upper limit, although quaternary compounds containing a total of 70 carbon atoms are contemplated. Generally, the total number of carbon atoms in the quaternary salt compound will be in the range of from 12 to 35 carbon atoms.

Non-limiting examples of organic quaternary salts include: Tetramethyl ammonium bromide, tetramethyl ammonium chloride, tetraethyl ammonium bromide, tetraethyl ammonium chloride, tetraethyl ammonium iodide, benzyltriethyl ammonium chloride, tetrapropyl ammonium bromide, tetrapropyl ammonium chloride, tetrapropyl ammonium iodide, triethylmethyl ammonium iodide, triethylpropyl ammonium iodide, tetrabutyl ammonium bromide, tetraabutyl ammonium chloride, tetrabutyl ammonium hydrogen sulfate, tributylmethyl ammonium iodide, benzyltributyl ammonium chloride, tributylpropyl ammonium iodide, tetrahexyl ammonium bromide, tetrapentyl ammonium bromide, tetraisopentyl ammonium iodide, tetrahexyl ammonium chloride, trioctyl methyl ammonium chloride, trioctylmethyl ammonium chloride, trioctylpropyl ammonium bromide, tetradecyl trimethyl ammonium bromide, trioctylpropyl ammonium bromide, cetyldimethylethyl ammonium bromide, cetyltrimethyl ammonium chloride, dimethyldicetyl ammonium chloride, didodecyldimethyl ammonium bromide, tetraheptyl ammonium bromide, hexa ($C_1$–$C_4$ alkyl) guanidinium chloride salts, tributylhexadecyl phosphonium bromide, tetrabutyl phosphonium chloride and tetraethyl phosphonium bromide.

Other analogous organic quaternary salts may be similarly named by substituting another halide, i.e., chloride, bromide or iodide, for the halide specifically name in the aforesaid examples, and/or by substituting other alkyl, cycloalkyl, alkylaryl, or aryl groups containing from 1 to 25 carbon atoms for the alkyl groups specifically name. In addition, phosphonium compounds corresponding to the quaternary ammonium salts described above can also be used, i.e., phosphorus can be substituted for the nitrogen in the quaternary ammonium salts named and vice versa. Such other quaternary ammonium or phosphonium salts are contemplated herein although they are not specifically enumerated. Mixtures of two or more of the above-described organic quaternary salts can be used as the catalyst in the process described herein.

Many organic quaternary ammonium salts are available commercially. The quaternary ammonium or phosphonium salts can be prepared readily by alkylation of the corresponding primary, secondary or tertiary amine or phosphine. The alkylation reaction is usually conducted by heating (at 50–100° C.) stoichiometric amounts of the corresponding amine (or phosphine) with the appropriate hydrocarbon halide, hydrogen sulfate or dihydrogen phosphate in a polar solvent such as methanol or acetonitrile for a few hours or days.

Other nucleophilic catalysts that may be used include crown ether, cryptand, spherand or calixarene complexes of organic or inorganic salts. These are discussed in "March's Advanced Organic Chemistry, reactions, Mechanisms and Structures", 5$^{th}$ Edition, M. B. Smith and J. March, Wiley-Interscience, 2001, pages 105–109, which discussion is incorporated herein by reference. Crown ethers are large ring compounds containing several oxygen atoms, usually in a regular pattern. Examples are 12-crown-4 (where 12 is the size of the ring and 4 represents the number of coordinating atoms, e.g., oxygen), dicyclohexano-18-crown-6, and 15-crown-5. The crown ethers have the property of forming complexes with positive ions, such as ammonium or substituted ammonium ions. Crown ethers, cryptates and calixarenes are all commercially available.

Other compounds than can be used as the nucleophilic catalyst include, but are not limited to, those compounds that react with chloroformates to form organic salts. Non-limiting examples of compounds that can serve as the nucleophilic catalyst include tertiary amines, such as triethylamine, tributylamine, pyridine, N, N-dimethylaniline and imidazole; amides, such as dimethylformamide; substituted ureas and thioureas, more particularly tetraalkyl(thio) ureas, such as tetrabutylurea and tetrabutylthiourea; tertiary phosphines, particularly aliphatic tertiary phosphines such as trioctylphosphine; and substituted phosphoramides, e.g., hexamethylphosphotriamide. Mixtures of nucleophilic catalysts can, of course, be used when the catalysts chosen are not chemically reactive with one another.

In one embodiment, the tertiary amines can be more graphically illustrated by the following formula:

IV

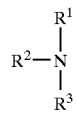

wherein $R^1$, $R^2$, and $R^3$ in formula IV are each monovalent hydrocarbon groups containing from 1 to 25 carbon atoms, as for example, $C_1$–$C_{20}$ alkyl groups; $C_5$–$C_6$ cycloalkyl groups; aryl groups such as phenyl and p-tolyl; or alkylaryl groups such as phenyl-substituted alkyl groups containing from 1 to 20 carbon atoms, e.g., benzyl, phenethyl, phenpropyl and phenbutyl. The tertiary amines of formula IV may also be depicted herein by the expression ($R^1R^2R^3N$). Other tertiary amines that can be used as the catalyst include 5 and 6 member monocyclic heteroatomic ring compounds containing at least one, e.g., 1 or 2, tertiary nitrogen atoms, such as pyridine and imidazole, i.e., wherein the hetero atom(s) is nitrogen.

The number of carbon atoms in each of the hydrocarbon substituents, $R^1$, $R^2$, and $R^3$ in formula IV can vary considerably. Each can contain from 1 to 25 or more carbon atoms. Typically, each hydrocarbon group will contain from 1 to 18 carbon atoms. In the case of certain alkyl hydrocarbon groups containing 8 or more carbon atoms, the number of carbon atoms in the group may be an average number, i.e., the hydrocarbon groups contains a distribution of alkyl groups of varying carbon length.

The total carbon atom content of all of the groups, $R^1$, $R^2$, and $R^3$, in formula IV will in one embodiment be at least 4. The upper limit of the number of carbon atoms will depend on economic and other practical factors. An upper total limit of 40 carbon atoms is a practical upper limit, although tertiary amine compounds containing a total of 70 carbon atoms are contemplated. Generally, the total number of carbon atoms in the tertiary amine compound will be in the range of from 4 to 35 carbon atoms.

Other nucleophilic compounds include tertiary phosphines and especially aliphatic tertiary phosphines, such as trioctylphosphine. The tertiary phosphines can be more graphically illustrated by the following formula:

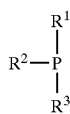

(V)

wherein $R^1$, $R^2$, and $R^3$ in formula V are each monovalent hydrocarbon groups containing from 1 to 25 carbon atoms, as for example, $C_1$–$C_{20}$ alkyl groups; $C_5$–$C_6$ cycloalkyl groups; aryl groups such as phenyl and p-tolyl; or alkylaryl groups such as phenyl-substituted alkyl groups containing from 1 to 20 carbon atoms, e.g., benzyl, phenethyl, phenpropyl and phenbutyl. The tertiary phosphines of formula V may also be depicted herein by the expression $(R^1R^2R^3P)$.

The number of carbon atoms in each of the hydrocarbon substituents, $R^1$, $R^2$, and $R^3$ in formula V can vary considerably. Each can contain from 1 to 25 or more carbon atoms. Typically, each hydrocarbon group will contain from 1 to 18 carbon atoms. In the case of certain alkyl hydrocarbon groups containing 8 or more carbon atoms, the number of carbon atoms in the group may be an average number, i.e., the hydrocarbon groups contains a distribution of alkyl groups of varying carbon length.

The total carbon atom content of all of the groups, $R^1$, $R^2$, and $R^3$, in formula V will in one embodiment be at least 4. The upper limit of the number of carbon atoms will depend on economic and other practical factors. An upper total limit of 40 carbon atoms is a practical upper limit, although tertiary phosphine compounds containing a total of 60 carbon atoms are contemplated. Generally, the total number of carbon atoms in the tertiary phosphine compound will be in the range of from 4 to 35 carbon atoms.

Other nucleophilic compounds that can serve as the catalyst include amides, such as dimethylformamide. The amides can be more graphically illustrated by the following formula:

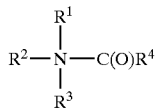

(VI)

wherein $R^1$, $R^2$, $R^3$ and $R^4$ in formula VI are each selected from hydrogen and monovalent hydrocarbon groups containing from 1 to 25 carbon atoms, as for example, $C_1$–$C_{20}$ alkyl groups; $C_5$–$C_6$ cycloalkyl groups; aryl groups such as phenyl and p-tolyl; or alkylaryl groups such as phenyl-substituted alkyl groups containing from 1 to 20 carbon atoms, e.g., benzyl, phenethyl, phenpropyl and phenbutyl.

The number of carbon atoms in each of the hydrocarbon substituents, $R^1$, $R^2$, $R^3$ and $R^4$ in formula VI can vary considerably. Each can contain from 1 to 25 or more carbon atoms. Typically, each hydrocarbon group will contain from 1 to 18 carbon atoms. In the case of certain alkyl hydrocarbon groups containing 8 or more carbon atoms, the number of carbon atoms in the group may be an average number, i.e., the hydrocarbon groups contains a distribution of alkyl groups of varying carbon length.

The total carbon atom content of all of the groups, $R^1$, $R^2$, $R^3$ and $R^4$, in formula VI will in one embodiment be at least 4. The upper limit of the number of carbon atoms will depend on economic and other practical factors. Generally, the total number of carbon atoms in the amide compound will be in the range of from 4 to 35 carbon atoms.

Other nucleophilic compounds that can serve as the catalyst include substituted ureas and thioureas and more particularly tetraalkyl(thio)ureas, such as tetrabutylurea and tetrabutylthiourea. The ureas and thioureas can be more graphically illustrated by the following formula:

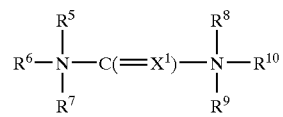

(VII)

wherein $X^1$ is oxygen or sulfur, and $R^5$, $R^6$, $R^7$, $R^8$, $R^9$ and $R^{10}$ in formula VII are each selected from hydrogen and monovalent hydrocarbon groups containing from 1 to 25 carbon atoms, as for example, $C_1$–$C_{20}$ alkyl groups; $C_5$–$C_6$ cycloalkyl groups; aryl groups such as phenyl and p-tolyl; or alkylaryl groups such as phenyl-substituted alkyl groups containing from 1 to 20 carbon atoms, e.g., benzyl, phenethyl, phenpropyl and phenbutyl.

The number of carbon atoms in each of the hydrocarbon substituents, $R^5$, $R^6$, $R^7$, $R^8$, $R^9$ and $R^{10}$ in formula VII can vary considerably. Each can contain from 1 to 25 or more carbon atoms. Typically, each hydrocarbon group will contain from 1 to 18 carbon atoms. In the case of certain alkyl hydrocarbon groups containing 8 or more carbon atoms, the number of carbon atoms in the group may be an average number, i.e., the hydrocarbon groups contains a distribution of alkyl groups of varying carbon length. The upper limit of the number of carbon atoms will depend on economic and other practical factors. Generally, the total number of carbon atoms in the urea or thiourea compound will be in the range of from 3 to 35 carbon atoms.

Other nucleophilic compounds that can serve as the catalyst include substituted phosphoramides and more particularly hexaalkyl phosphoramides, such as hexamethylphosphotriamide. The phosphoramides can be more graphically illustrated by the following formula:

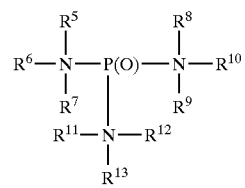

wherein $R^5$, $R^6$, $R^7$, $R^8$, $R^9$, $R^{10}$, $R^{11}$, $R^{12}$, and $R^{13}$ in formula VIII are each selected from hydrogen and monovalent hydrocarbon groups containing from 1 to 25 carbon atoms, as for example, $C_1$–$C_{20}$ alkyl groups; $C_5$–$C_6$ cycloalkyl groups; aryl groups such as phenyl and p-tolyl; or alkylaryl groups such as phenyl-substituted alkyl groups containing from 1 to 20 carbon atoms, e.g., benzyl, phenethyl, phenpropyl and phenbutyl.

The number of carbon atoms in each of the hydrocarbon substituents, $R^5$, $R^6$, $R^7$, $R^8$, $R^9$ and $R^{10}$ in formula VIII can vary considerably. Each can contain from 1 to 25 or more carbon atoms. Typically, each hydrocarbon group will contain from 1 to 18 carbon atoms. In the case of certain alkyl hydrocarbon groups containing 8 or more carbon atoms, the number of carbon atoms in the group may be an average number, i.e., the hydrocarbon groups contains a distribution of alkyl groups of varying carbon length. The upper limit of the number of carbon atoms will depend on economic and other practical factors. Generally, the total number of carbon atoms in the phosphoramide compound will be in the range of from 6 to 35 carbon atoms.

Still other nucleophilic compounds include alkyl substituted guanidines and hexasubstituted guanidinium halides, which may be graphically illustrated respectively by the following formulae:

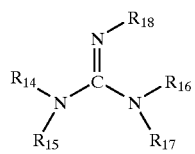

(IX)

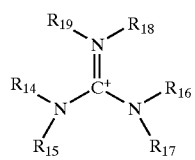

(X)

wherein $X_2$ is chloro or bromo, particularly chloro, and $R_{14}$–$R_{19}$ are the same or different, and each are hydrogen or a $C_1$–$C_8$ alkyl group, particularly a $C_1$–$C_4$ alkyl group, such as methyl, ethyl, propyl or butyl.

Non-limiting examples of such guanidine and guanidinium halide compounds include: tetrasubstituted guanidine, e.g., tetraalkyl guanidine such as tetrabutyl guanidine; pentasubstituted guanidine, e.g., pentaalkyl guanidine and their hydrogen halide, e.g., hydrochloride, salts, guanidine and the hydrogen chloride salt of pentabutyl guanidine; hexasubstituted guanidinium chloride or bromide, e.g., hexaalkyl guanidinium chloride or bromide such as hexaethyl guanidinium chloride and hexabutylguanidinium chloride.

The foregoing guanidine and guanidinium halide compounds can be prepared by the methods described in U.S. Pat. No. 5,712,407, column 6, line 45 to column 7, line 56.

The amount of catalyst required for the process of the invention is that amount that will catalyze the decomposition of the chloroformate contaminants; namely, methyl chloroformate, dichloromethyl chloroformate and trichloromethyl chloroformate (if present), i.e., a catalytic amount. More particularly, the amount of catalyst utilized is at least 0.001 weight percent, based on the total weight of the crude chloroformate mixture, but less than an equivalent amount (based on the amount of chloroformate). The amount of catalyst used can vary from 0.001 to 1 weight percent, e.g., from 0.01 to 0.8 weight percent, or 0.1 to 0.5 weight percent. The amount of catalyst used can range from any combination of the recited catalyst amounts, inclusive of the recited amounts. Generally, the lower the amount of catalyst used, the longer the heating time required to remove the contaminating chloroformates from the crude chloroformate mixture, and vice versa. In an embodiment of the present invention, a level of catalyst used is chosen so that the period of time utilized to remove the contaminating chloroformates, i.e., to non-detectable levels (as measured by GC), is from 30 minutes to from 2 to 3 hours.

The process of the present invention is more particularly described in the following examples, which are intended as illustrative only since numerous modifications and variations therein will be apparent to those skilled in the art.

In the following examples, crude chloroformate mixtures comprising chloromethyl chloroformate (CMC), methyl chloroformate (MCF) and dichloromethyl chloroformate (DCMC) were used. The chloroformate mixtures were obtained by the catalytic chlorination of methyl chloroformate. An example of such a chlorination reaction is found in Example 1. The chloroformate composition of crude chlorination reaction mixtures that have been prepared as in Example 1 will vary. Further, when stored, the crude chlorination reaction mixture will also change over time.

Analyses of the crude chloroformate mixtures and products resulting from the described processes in the following examples were performed by gas chromatography (GC). A Hewlett Packard 6890 Gas Chromatograph was used with a capillary column. A thermal conductivity detector (TCD) was used unless otherwise specified. When so specified, a flame ionization detector (FID) was used. All GC analyses are reported as area %.

EXAMPLE 1

(Chlorination of Methyl Chloroformate)

Methyl chloroformate (MCF, 1628.9 grams) and 2,2'-azobisisobutyronitrile (AIBN, 10.32 grams) were added to a 2-liter flask purged with nitrogen gas and topped with a water-cooled condenser. The mixture was heated with a heating mantel to 70° C. (A thermocouple was immersed in the reaction medium to measure its temperature.) Subnatent addition of chlorine gas was started and after 2 hours of chlorine addition at 70° C., 4.8 grams of additional AIBN was added. After 2 hours of further chlorine addition, 5.9 grams of additional AIBN was added and chlorine addition was continued for another hour. Then, 3.2 grams of AIBN was added and the chlorination reaction continued for an additional 1.5 hours. Then 4.4 grams of AIBN was added and the chlorination was continued for an additional 4 hours, at which time the chlorination reaction was discontinued. The crude reaction mixture was analyzed by GC (FID detector). GC analyses found chloromethyl chloroformate (CMC, 68.5 area %), dichloromethyl chloroformate (DCMC, 1.94 area %) and methyl chloroformate (MCF, 15.2 area %).

EXAMPLE 2

A crude chloroformate mixture (268 grams) comprising CMC, (74.4 area %), MCF (14.1%), and DCMC (2.21 area %) was mixed with benzyltributyl ammonium chloride (6.7 grams) in a 250 milliliter (mL) flask equipped with a thermometer, water-cooled condenser and gas inlet. A gentle subnatent nitrogen sparge was maintained during the subsequent heating step. The flask was slowly heated to 96° C. with a heating mantel and maintained at from 96° C. to 100° C. for 1 hour. The contents of the flask were analyzed by GC and found to contain 0.2% MCF and 0.02% DCMC. Vacuum distillation of the contents of the flask using a short Vigreux column (52–55° C. @ 100 Torr) resulted in a distilled product (178.4 grams) that when analyzed by GC was found to be 97.8% pure (CMC) and to contain 0.08 area % MCF and 0.0 area % DCMC. The remainder of the product was unidentified components, presumed to be unidentified lights and heavies. Vacuum distillation was performed so that the yield for the decomposition process could be measured directly.

EXAMPLE 3

A crude chloroformate mixture (1503.2 grams) comprising CMC (69.7 area %), MCF (4.2 area %) and DCMC (19.7 area %) was mixed with tricaprylylmethyl ammonium chloride [ALIQUAT® 336 (17.67 grams)] and heated in a jacketed, stirred (100–200 rpm), baffled 2-liter glass flask equipped with thermometer and water-cooled condenser. The flask was heated at 73–79° C. for 4.3 hours and then the temperature was raised from 79° C. to 90° C. over a 2 hour period. The contents of the flask, which then weighed 1049 grams, was analyzed by GC and found to contain 0.51 area % MCF and 0.0 area % DCMC.

EXAMPLE 4

A crude chloroformate mixture (13.61 grams) comprising CMC (69.8 area %), and MCF (21.1 area %) was mixed with hexaethyl guanidinium chloride (0.0973 grams). The mixture was heated in a 10 mL flask equipped with a water-cooled condenser. The flask was lowered into an 85° C. oil bath. After 35 minutes at 85° C., the oil bath temperature was raised to 90° C. After 45 minutes at 90° C., the oil bath temperature was raised to 100° C. After 30 minutes at 100° C., the mixture in the flask was sampled and analyzed by GC. The sample was found to contain 0.28 area % of MCF. The contents of the flask were held an additional 90 minutes at 100° C. and then re-analyzed by GC. The contents of the flask (8.83 grams) were found to contain 0.008 area % MCF.

EXAMPLE 5

A crude chloroformate mixture (13.13 grams) comprising CMC (69.8 area %) and MCF (21.1 area %) was mixed with hexadecyl tributyl phosphonium bromide (0.2022 grams) in a 10 mL flask equipped with a water-cooled condenser. The flask was lowered into an 85° C. oil bath. After 35 minutes at 85° C., the oil bath temperature was raised to 90° C. After 25 minutes at 90° C., the contents of the flask was sampled and found to contain 3.3 area % MCF by GC. After an additional 20 minutes at 90° C., the oil bath temperature was raised to 100° C. After 100 minutes at 100° C., the contents of the flask (8.83 grams) were re-analyzed by GC and found to contain 0.12 area % MCF.

EXAMPLE 6

A crude chloroformate mixture (12.5 grams) comprising CMC (69.8 area %), MCF (21.1 area )% and DCMC (2.69 area %) was mixed with dibenzo-18-crown-6 (0.157 grams) and potassium fluoride (0.162 grams) in a 10 mL flask equipped with a water-cooled condenser. The flask was lowered into a 90° C. oil bath. After 80 minutes at 90° C., the contents of the flask were sampled and analyzed by GC. The amount of MCF and DCMC were found to be 19.5 area % and 1.85 area % respectively. After an additional 50 minutes at 90° C., the oil bath temperature was raised to 95° C. After 50 minutes at 95° C., the contents of the flask were again sampled and analyzed by GC. This analysis found the MCF and DCMC to be 16.7 area % and 1.25 area % respectively. After an additional 16 hours at 95° C., the contents of the flask (8.65 grams) were sampled and analyzed by GC. The levels of MCF and DCMC were found to be 2.26 area % and 0.03 area % respectively.

EXAMPLE 7

A crude chloroformate mixture (9.938 grams) comprising CMC (69.8 area %), MCF (21.1 area %) and DCMC (2.69 area %) was mixed with DOWEX® SBR resin [ionic form hydroxide, dry mesh (16–40 US Sieve mesh) (0.368 grams) in a 10 mL flask equipped with a water-cooled condenser. The flask was lowered into a 90° C. oil bath. After 80 minutes at 90° C., the oil bath temperature was raised to 95° C. After 17 hours at 95° C., the contents of the flask (5.00 grams) were sampled and analyzed by GC. The level of MCF and DCMC were found to be 1.10 area % and 0.09 area % respectively.

EXAMPLE 8

A crude chloroformate mixture (11.75 grams) comprising CMC (70 area %), MCF (19.4 area %) and DCMC (1.12 area %) was mixed with tetraethyl ammonium iodide (0.254 grams) in a 10 mL flask equipped with a water-cooled condenser. The flask was lowered into an 85° C. oil bath. After 30 minutes at 85° C., the oil bath temperature was raised to 90° C. After 30 minutes at 90° C., the oil bath temperature was raised to 95° C. After 15 minutes at 95° C., the contents of the flask were sampled and analyzed by GC. The analyses showed 7.92 area % MCF and 0.18 area % DCMC. The contents of the flask were held at 95° C. for an additional 40 minutes and then sampled and analyzed by GC. The levels of MCF and DCMC were found to be 7.60 area % and 0.07 area % respectively. The oil bath temperature was then raised to 110° C. and held there for 40 minutes, whereupon the contents of the flask (8.60 grams) were again sampled and analyzed by GC. The levels of MCF and DCMC were found to be 0.0 area % and 0.01 area % respectively.

EXAMPLE 9

A crude chloroformate mixture (11.40 grams) comprising CMC (70.0 area %), MCF (19.4 area %) and DCMC (1.12 area %) was mixed with 1-(N,N-dimethylcarbamoyl)-4-(2-sulfoethyl) pyridinium hydroxide, inner salt (0.200 grams) in a 10 mL flask equipped with a water-cooled condenser. The flask was lowered into an 85° C. oil bath. After 30 minutes at 85° C., the oil bath temperature was raised to 90° C. After 30 minutes at 90° C., the contents of the flask were sampled and analyzed by GC. The amounts of MCF and DCMC found were 9.65 area % and 0.05 area % respectively. The oil bath temperature was then raised to 95° C. After 45 minutes at 95° C., the contents of the flask were sampled and analyzed by GC. The levels of MCF and DCMC found were 1.77 area % and 0.01 area % respectively. The oil bath temperature was then raised to 110° C. and the flask maintained at that temperature for 40 minutes, whereupon the contents of the flask (7.79 grams) were sampled again and analyzed by GC. The levels of MCF and DCMC found were 0.02 area % and 0.02 area % respectively.

EXAMPLE 10

A crude chloroformate mixture (13.78 grams) comprising CMC (70.2 area %), MCF (22.8 area %) and DCMC (2.76 area %) was mixed with 0.0164 grams of benzyltributyl ammonium chloride (BTBAC) in a 10 mL flask equipped with a water-cooled condenser. The flask was lowered in a 100° C. oil bath. After one hour at 100° C., the contents of the flask were sampled and analyzed by GC. The levels of MCF and DCMC found were 9.4 area % and 0.23 area % respectively. After an additional 1 hour at 100° C., the contents of the flask were sampled again and analyzed by GC. The levels of MCF and DCMC found were 0.65 area % and 0.01 area % respectively. The oil bath temperature was then raised to 105° C. and the contents of the flask held at this temperature for one hour. The contents of the flask (9.55 grams) were again sampled and analyzed by GC. The levels of MCF and DCMC found were 0.05 area % and 0.01 area % respectively. The product was found to be 98.8 area percent CMC (by GC).

EXAMPLE 11

A crude chloroformate mixture (14.14 grams) comprising CMC (70.1 area %), MCF (21.9 area %) and DCMC (2.16 area %) was mixed with BTBAC ((0.129 grams) in a 10 mL flask equipped with a water-cooled condenser. The flask was lowered into an 80° C. oil bath and after 277 minutes at that temperature, the flask was removed from the oil bath and its contents sampled and analyzed by GC. The levels of MCF and DCMC found were 0.03 area % and 0.01 area % respectively. The flask contained 9.99 grams of crude product (98.1 area % CMC by CC).

EXAMPLE 12

A crude chloroformate mixture (14.47 grams) comprising CMC (68.8 area %), MCF (19.4%) and DCMC (0.54%) was mixed with N,N-dimethylformamide (0.315 grams) and the mixture heated in a 10 mL flask equipped with a water-cooled condenser. The flask was lowered into a 90° C. oil bath. After 110 minutes at 90° C., the mixture in the flask was sampled and analyzed by GC. The sample was found to contain MCF (0.00 area %), CMC (91.1 area %) and DCMC (0.19 area %).

EXAMPLE 13

A crude chloroformate mixture (13.40 grams) comprising CMC (69.8 area %), MCF (21.1 area %) and DCMC (1.90 area %) was mixed with 0.8 weight percent of BTBAC in a 10 mL flask equipped with a water-cooled condenser and a gas inlet tube that extended below the surface of the flask contents. The flask was lowered into an 85° C. oil bath and nitrogen was introduced into the gas inlet tube, thereby to provide a gentle subsurface nitrogen sparge. After 60 minutes at 85° C., the contents of the flask were sampled and analyzed by GC. The levels of MCF and DCMC found were 0.22 area % and 0.01 area % respectively.

The preceding procedure was performed simultaneously in a similar 10 mL flask with a crude chloroformate mixture (13.96 grams) having MCF (21.3 area %) and DCMC (1.64 area %), but with 0.9 weight percent BTBAC, no nitrogen sparge, and for an 80 minute residence time in the oil bath. The contents of the flask were sampled and analyzed by GC. The levels of MCF and DCMC were found to be 5.1 area % and 0.06 area % respectively.

This example demonstrates the benefit of an inert gas sparge to assist in the removal of gaseous decomposition products from the vicinity of the crude chloroformate mixture during the heating step.

While the invention has been described in detail with respect to certain embodiments thereof, it is to be understood that the invention is not intended to be limited to such details except as and insofar as they appear in the appended claims.

What is claimed is:

1. A method of removing methyl chloroformate from a chloroformate mixture comprising chloromethyl chloroformate and a contaminating amount of methyl chloroformate, which method comprises (a) heating said mixture in a reaction zone in the presence of a catalytic amount of nucleophilic catalyst, (b) simultaneously removing volatile gaseous products resulting from step (a) from said reaction zone, and (c) recovering chloromethyl chloroformate substantially free of methyl chloroformate from said reaction zone.

2. The method of claim 1 wherein the chloroformate mixture further comprises dichloromethyl chloroformate.

3. The method of claim 1 wherein the temperature at which the chloroformate mixture is heated ranges from at least 50° C. to the reflux temperature of the mixture in the reaction zone.

4. The method of claim 3 wherein chemically inert gas is introduced into the reaction zone to assist in the removal of the volatile gaseous products from said reaction zone.

5. The method of claim 1 wherein the reaction zone is maintained at sub-atmospheric pressures during steps (a) and (b).

6. The method of claim 5 wherein the sub-atmospheric pressure ranges from 50 Torr to 720 Torr.

7. The method of claim 4 wherein the reaction zone is maintained at sub-atmospheric pressures during steps (a) and (b).

8. The method of claim 7 wherein the sub-atmospheric pressure ranges from 50 Torr to 720 Torr.

9. The method of claim 1 wherein the nucleophilic catalyst is selected from quaternary ammonium salts, quaternary phosphonium salts, and crown ether, cryptand, spherand or calixarene complexes of organic or inorganic salts.

10. The method of claim 1 wherein the catalyst is a quaternary ammonium or phosphonium salt.

11. The method of claim 10 wherein the catalyst is represented by the following general formulae:

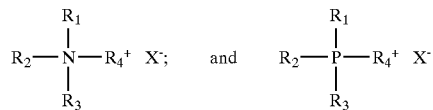

wherein $R_1$, $R_2$, $R_3$ and $R_4$ are each monovalent hydrocarbon groups containing from 1 to 25 carbon atoms, and X is a monovalent anion.

12. The method of claim 11 wherein the total number of carbon atoms in the monovalent hydrocarbon groups ranges from 12 to 35, and the monovalent anion is selected from a halide anion, hydrogen sulfate anion, hydroxyl anion, dihydrogen phosphate anion, and hydrogen phosphate anion.

13. The method of claim 12 wherein the halide anion is a chloride or bromide.

14. The method of claim 4 wherein inert gas introduced into the reaction zone comprises nitrogen.

15. A method for recovering chloromethyl chloroformate from a chloroformate mixture comprising chloromethyl chloroformate, methyl chloroformate and dichloromethyl chloroformate, which method comprises heating said chloroformate mixture in a reaction zone in the presence of a catalytic amount of nucleophilic catalyst, (b) simultaneously removing volatile gaseous products produced in step (a) from said reaction zone, and (c) recovering chloromethyl chloroformate product substantially free of methyl chloroformate and dichloromethyl chloroformate.

16. The method of claim 15 wherein the chloroformate mixture further comprises trichloromethyl chloroformate.

17. The method of claim 15 wherein the chloroformate mixture is heated at temperatures of from greater than 70° C. to the reflux temperature of the mixture in the reaction zone.

18. The method of claim 15 wherein the chloroformate mixture is heated at temperatures of from 86° C. to 100° C.

19. The method of claim 17 wherein chemically inert gas is introduced into the reaction zone to assist in the removal of volatile gaseous products from said reaction zone.

20. The method of claim 19 wherein the volatile gaseous products include hydrogen chloride and the inert gas comprises nitrogen.

21. The method of claim 15 wherein the chloromethyl chloroformate product comprises at least 95% chloromethyl chloroformate, less than 5% methyl chloroformate and less than 2% dichloromethyl chloroformate, as determined by gas chromatography analysis.

22. The method of claim 15 wherein the chloromethyl chloroformate product comprises at least 98% chloromethyl chloroformate, less than 1% methyl chloroformate and less than 1% dichloromethyl chloroformate, as determined by gas chromatography analysis.

23. The method of claim 17 wherein the reaction zone is maintained at sub-atmospheric pressures during steps (a) and (b).

24. The method of claim 17 wherein the catalyst is a quaternary ammonium or phosphonium salt.

25. The method of claim 24 wherein the salt is a chloride or bromide salt.

26. A method comprising the steps of (a) heating a chloroformate mixture comprising chloromethyl chloroformate and contaminating amounts of methyl chloroformate in a reaction zone at temperatures of from at least 50° C. to the reflux temperature of the mixture in the reaction zone in the presence of a catalytic amount of nucleophilic catalyst, (b) simultaneously removing volatile gaseous products including hydrogen chloride resulting from step (a) from said reaction zone, and (c) recovering chloromethyl chloroformate product substantially free of methyl chloroformate from said reaction zone.

27. The method of claim 26 wherein the chloroformate mixture further comprises contaminating amounts of dichloromethyl chloroformate, and the chloromethyl chloroformate product is substantially free of dichloromethyl chloroformate.

28. The method of claim 26 wherein the nucleophilic catalyst is a quaternary ammonium or phosphonium salt.

29. The method of claim 27 wherein the nucleophilic catalyst is represented by the following general formulae:

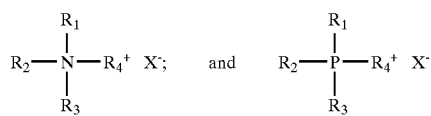

wherein $R_1$, $R_2$, $R_3$ and $R_4$ are each monovalent hydrocarbon groups containing from 1 to 25 carbon atoms, and X is a monovalent anion.

30. The method of claim 29 wherein the total number of carbon atoms in the monovalent hydrocarbon groups ranges from 12 to 35, and the monovalent anion is selected from a halide anion, hydrogen sulfate anion, hydroxyl anion, dihydrogen phosphate anion, and hydrogen phosphate anion.

31. The method of claim 30 wherein the halide anion is a chloride or bromide.

32. The method of claim 29 wherein chemically inert gas is introduced into the reaction zone to assist in the removal of the volatile gaseous products.

33. The method of claim 29 wherein the reaction zone is maintained at sub-atmospheric pressures during steps (a) and (b).

34. The method of claim 32 wherein the inert gas comprises nitrogen.

35. The method of claim 34 wherein the inert gas is introduced directly into the chloroformate mixture.

36. The method of claim 29 wherein the chloromethyl chloroformate product comprises at least 98% chloromethyl chloroformate, less than 1% methyl chloroformate and less than 1% dichloromethyl chloroformate, as determined by gas chromatography analysis.

37. The method of claim 1 wherein the nucleophilic catalyst is selected from tertiary amines, amides, substituted ureas and thioureas, tertiary phosphines and substituted phosphoramides.

38. The method of claim 37 wherein the nucleophilic catalyst is selected from triethylamine, tributyl amine, pyridine, N,N-dimethylaniline, imidazole, dimethylformamide, tetrabutylurea, tetrabutylthiourea, trioctylphosphine, and hexamethylphosphotriamide.

39. The method of claim 15 wherein the nucleophilic catalyst is selected from tertiary amines, amides, substituted ureas and thioureas, tertiary phosphines and substituted phosphoramides.

40. The method of claim 39 wherein the nucleophilic catalyst is selected from triethylamine, tributyl amine, pyridine, N,N-dimethylaniline, imidazole, dimethylformamide, tetrabutylurea, tetrabutylthiourea, trioctylphosphine, and hexamethylphosphotriamide.

41. The method of claim 26 wherein the nucleophilic catalyst is selected from tertiary amines, amides, substituted ureas and thioureas, tertiary phosphines and substituted phosphoramides.

42. The method of claim 41 wherein the nucleophilic catalyst is selected from triethylamine, tributyl amine, pyridine, N,N-dimethylaniline, imidazole, dimethylformamide, tetrabutylurea, tetrabutylthiourea, trioctylphosphine, and hexamethylphosphotriamide.

43. The method of claim 1 wherein the nucleophilic catalyst is selected from alkyl substituted guanidines and hexasubstituted guanidinium halides.

44. The method of claim 43 wherein the nucleophilic catalyst is selected from tetrabutyl guanidine, pentabutyl guanidine, pentabutyl guanidine hydrogen chloride salt, hexaethyl guanidinium chloride and hexabutylguanidinium chloride.

45. The method of claim 15 wherein the nucleophilic catalyst is selected from alkyl substituted guanidines and hexasubstituted guanidinium halides.

46. The method of claim 45 wherein the nucleophilic catalyst is selected from tetrabutyl guanidine, pentabutyl guanidine, pentabutyl guanidine hydrogen chloride salt, hexaethyl guanidinium chloride and hexabutylguanidinium chloride.

47. The method of claim 26 wherein the nucleophilic catalyst is selected from alkyl substituted guanidines and hexasubstituted guanidinium halides.

48. The method of claim 47 wherein the nucleophilic catalyst is selected from tetrabutyl guanidine, pentabutyl guanidine, pentabutyl guanidine hydrogen chloride salt, hexaethyl guanidinium chloride and hexabutylguanidinium chloride.

* * * * *